(12) United States Patent
Born et al.

(10) Patent No.: US 12,281,373 B2
(45) Date of Patent: Apr. 22, 2025

(54) WIRES OF NICKEL-TITANIUM ALLOY AND METHODS OF FORMING THE SAME

(71) Applicant: W. L. Gore & Associates, Inc., Newark, DE (US)

(72) Inventors: Debra K. Born, Flagstaff, AZ (US); Parikshith K. Kumar, Flagstaff, AZ (US); Kehinde A. Majolagbe, Flagstaff, AZ (US); Jared S. Nelson, Flagstaff, AZ (US); James D. Silverman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 364 days.

(21) Appl. No.: 17/764,384

(22) PCT Filed: Sep. 25, 2020

(86) PCT No.: PCT/US2020/052766
§ 371 (c)(1),
(2) Date: Mar. 28, 2022

(87) PCT Pub. No.: WO2021/062186
PCT Pub. Date: Apr. 1, 2021

(65) Prior Publication Data
US 2022/0290275 A1 Sep. 15, 2022

Related U.S. Application Data

(60) Provisional application No. 62/907,490, filed on Sep. 27, 2019.

(51) Int. Cl.
| | |
|---|---|
| *C22C 14/00* | (2006.01) |
| *A61B 17/00* | (2006.01) |
| *A61F 2/01* | (2006.01) |
| *A61F 2/07* | (2013.01) |
| *A61F 2/24* | (2006.01) |
| *C22C 19/00* | (2006.01) |
| *C22C 19/03* | (2006.01) |
| *C22F 1/00* | (2006.01) |
| *C22F 1/10* | (2006.01) |
| *C22F 1/18* | (2006.01) |

(52) U.S. Cl.
CPC .......... *C22C 14/00* (2013.01); *A61B 17/0057* (2013.01); *A61F 2/01* (2013.01); *A61F 2/07* (2013.01); *A61F 2/24* (2013.01); *C22C 19/007* (2013.01); *C22C 19/03* (2013.01); *C22F 1/006* (2013.01); *C22F 1/10* (2013.01); *C22F 1/183* (2013.01); *C22C 2200/00* (2013.01)

(58) Field of Classification Search
CPC .. C22C 14/00; C22F 1/006; C22F 1/10; C22F 1/183; A61B 17/0057; A61F 2/07; A61F 2/24
See application file for complete search history.

(56) References Cited

U.S. PATENT DOCUMENTS

| | | | |
|---|---|---|---|
| 4,707,196 | A | 11/1987 | Honma et al. |
| 5,411,476 | A | 5/1995 | Abrams et al. |
| 5,882,444 | A | 3/1999 | Flomenblit et al. |
| 6,217,567 | B1 | 4/2001 | Zadno-Azizi et al. |
| 7,455,738 | B2 | 11/2008 | Patel et al. |
| 7,789,979 | B2 | 9/2010 | Dooley et al. |
| 8,118,952 | B2 | 2/2012 | Gall et al. |
| 8,414,714 | B2 | 4/2013 | Schaffer |
| 8,888,838 | B2 | 11/2014 | Blanzy |
| 9,169,545 | B2 | 10/2015 | Padula et al. |
| 9,422,615 | B2 | 8/2016 | Greene et al. |
| 9,878,366 | B2 | 1/2018 | Johnson |
| 9,976,297 | B2 | 5/2018 | Danning |
| 12,043,881 | B2 | 7/2024 | Kumar |
| 2007/0293939 | A1 | 12/2007 | Shrivastava et al. |
| 2010/0075168 | A1 | 3/2010 | Schaffer |
| 2012/0282571 | A1 | 11/2012 | Ammon et al. |
| 2014/0242543 | A1 | 8/2014 | Johnson |
| 2018/0153718 | A1 | 6/2018 | Armstrong et al. |

(Continued)

FOREIGN PATENT DOCUMENTS

| | | |
|---|---|---|
| CN | 107080598 A | 8/2017 |
| CN | 110431246 A | 11/2019 |

(Continued)

OTHER PUBLICATIONS

Avery, Matthew, Benjamin Chui, and Julia Cross. "Reverse Engineering of Nitinol Vena Cava Filters." Material Science 102 (2000).*
Kajzer, W., et al. "Surface modification and corrosion resistance of Ni—Ti alloy used for urological stents." Journal of Achievements in Materials and Manufacturing Engineering 20.1-2 (2007): 123-126.
Laplanche, G., et al. "Effect of temperature and texture on the reorientation of martensite variants in NiTi shape memory alloys." Acta Materialia 127 (2017): 143-152.
International Preliminary Report on Patentability received for PCT Patent Application No. PCT/US2020/052766, mailed on Feb. 2, 2022, 17 pages.

(Continued)

*Primary Examiner* — Jessee R Roe (57) ABSTRACT

A wire of a nickel-titanium alloy having a permanent set of less than 5% when 11% strain is applied to the wire is disclosed. The wire may be formed by applying a first heat treatment to the wire, the first heat treatment includes applying heat of a first temperature for a first period of time, applying a strain deformation to the wire to set a shape for the wire during the first heat treatment, and applying a second heat treatment to the wire. The second heat treatment includes applying heat of a second temperature different from the first temperature for a second period of time, and the second temperature is between 210° C. and 290° C. The wire may have a modulus of at least 53 GPa when 200 MPa of stress is applied to the wire, and the wire is bonded to a secondary component.

40 Claims, 6 Drawing Sheets

(56) References Cited

U.S. PATENT DOCUMENTS

| | | |
|---|---|---|
| 2020/0209068 A1 | 7/2020 | Kise et al. |
| 2022/0349030 A1 | 11/2022 | Kumar |
| 2024/0336997 A1 | 10/2024 | Kumar |

FOREIGN PATENT DOCUMENTS

| | | | |
|---|---|---|---|
| JP | 09-078165 A | 3/1997 | |
| WO | 2010/051515 A1 | 5/2010 | |
| WO | 2014/078670 A1 | 5/2014 | |
| WO | 2016/012236 A1 | 1/2016 | |
| WO | WO-2016077777 A1 * | 5/2016 | ............. A61F 2/442 |

OTHER PUBLICATIONS

International Preliminary Report on Patentability received for PCT Patent Application No. PCT/US2020/052778, mailed on Feb. 2, 2022, 14 pages.

International Search Report and Written Opinion received for PCT Patent Application No. PCT/US2020/052766, mailed on Nov. 9, 2020, 12 pages.

International Search Report and Written Opinion received for PCT Patent Application No. PCT/US2020/052778, mailed on Nov. 12, 2020, 13 pages.

Khalil H. F. et al., "Changes in the Mechanical Behavior of Nitinol Following Variations of Heat Treatment Duration and Temperature," Georgia Institute of Technology, Dec. 2009, 59 pages.

Kim et al., "Ageing-induced two-stage R-phase transformation in Ti-50.9at.%Ni," Acta Materialia, vol. 52, 2004) 487-499.

Wang et al., "Effect of grain size on aging microstructure as reflected in the trnasformation behavior of a low-temperature aged Ti-50.8 at.% Ni alloy,"Scripta Materialia, vol. 69, Jul. 1, 2013, pp. 545-548.

Zhou et al., "Origin of 2-stage R-phase transformation in low-temperature aged Ni-rich Ti—Ni alloys,"Acta Materialia, vol. 53, Sep. 28, 2005, pp. 5365-5377.

Zhou et al., "Understanding of multi-stage R-phase transformation in aged Ni-rich Ti—Ni shape memory alloys," Materials Science and Engineering A, vol. 438-440, Nov. 25, 2006, pp. 602-607.

* cited by examiner

WIRES OF NICKEL-TITANIUM ALLOY AND METHODS OF FORMING THE SAME

CROSS-REFERENCE TO RELATED APPLICATION

This application is a national phase application of PCT Application No. PCT/US2020/052766, internationally filed on Sep. 25, 2020, which claims the benefit of Provisional Application No. 62/907,490, filed Sep. 27, 2019, which are incorporated herein by reference in their entireties for all purposes.

FIELD

The disclosure relates generally to metal alloys and methods of manufacturing the same.

BACKGROUND

There has been great interest in shape memory and superelastic alloys such as nickel-titanium. This family of alloys is also known as nitinol (i.e., Nickel-Titanium Naval Ordinance Laboratory). Key to exploiting the performance of nitinol alloys is the phase transformation in the crystalline structure that transitions between an austenitic phase and a martensitic phase. The austenitic phase is commonly referred to as the high temperature phase, and the martensitic phase is commonly referred to as the low temperature phase. The specific phase properties, and the repeatable change from one phase to the other is the mechanism for achieving unique superelasticity and shape memory properties of nitinol.

Nickel-titanium alloys are frequently used in medical devices for diagnosis and treatment. Minimally invasive implantation of medical devices, for example, may require a device that may be retracted to a smaller size for delivery to a target treatment site, and then released and expanded to a functional configuration, exploiting the superelastic and/or shape memory properties of nitinol. There is a need for enhancement in nitinol material properties and manufacturing process to produce nickel-titanium alloys with properties particularly suitable in medical devices where smaller retracted profile is preferred while maintaining or improving the properties of the medical devices at the expanded larger profile.

SUMMARY

Various disclosed concepts relate to a wire of a nickel-titanium alloy. According to one example ("Example 1"), a wire of a nickel-titanium alloy has a permanent set of less than 5% when 11% strain is applied to the wire.

According to another example ("Example 2") further to Example 1, the permanent set is less than 1% when the 11% strain is applied to the wire.

According to another example ("Example 3") further to Example 1 or 2, the wire has a modulus of at least 53 GPa when 200 MPa of stress is applied to the wire.

According to another example ("Example 4") further to Example 3, the modulus is at least 55 GPa.

According to another example ("Example 5") further to Example 3, the modulus is between 53 GPa and 64 GPa.

According to another example ("Example 6") further to any one of Examples 3 to 5, the modulus decreases by at least 5 GPa when 400 MPa of stress is applied to the wire.

According to another example ("Example 7") further to Example 6, the modulus decreases by at least 10 GPa when 400 MPa of stress is applied to the wire.

According to another example ("Example 8") further to Example 6, the modulus decreases by a value of between 5 GPa and 16 GPa when 400 MPa of stress is applied to the wire as compared to when 200 MPa of stress is applied to the wire.

According to another example ("Example 9") further to any preceding Example, the wire further a lower plateau stress (LPS) of at least 350 MPa.

According to another example ("Example 10") further to any preceding Example, the wire is formed into an implantable medical device.

According to another example ("Example 11") further to Example 10, the medical device is: a stent-graft, an embolic filter, a septal occluder, or a heart valve.

According to another example ("Example 12") a wire is formed by a method which includes applying a first heat treatment to the wire, applying a strain deformation to the wire during the first heat treatment to set a shape for the wire, and applying a second heat treatment to the wire. The first heat treatment includes applying heat of a first temperature for a first period of time. The second heat treatment includes applying heat of a second temperature different from the first temperature for a second period of time. The second temperature is between 210° C. and 290° C.

According to another example ("Example 13") further to Example 12, the first temperature is between 400° C. and 550° C.

According to another example ("Example 14") further to Example 12 or 13, the first heat treatment includes one or more additional heat treatment processes operable to set a shape of the wire.

According to another example ("Example 15") further to any one of Examples 12 to 14, the second period of time is between 5 minutes and 40 minutes.

According to another example ("Example 16") further to any one of Examples 12 to 15, a first elasticity of the wire resulting from the first heat treatment is within 2% of a second elasticity of the wire resulting from the second heat treatment.

According to another example ("Example 17") further to any one of Examples 12 to 16, a second hysteresis of the wire resulting from the second heat treatment is at least 40 MPa lower than a first hysteresis of the wire resulting from the first heat treatment.

According to another example ("Example 18") further to any one of Examples 12 to 17, a second lower plateau stress (LPS) of the wire resulting from the second heat treatment is at least 30 MPa higher than a first LPS of the wire resulting from the first heat treatment.

According to another example ("Example 19") further to any one of Examples 12 to 18, a second permanent set of the wire resulting from the second heat treatment is at least 85% lower than a first permanent set of the wire resulting from the first heat treatment, and each of the first and second permanent sets is defined by a length of the wire after a strain of 11% is applied to the wire.

According to another example ("Example 20") further to any one of Examples 12 to 18, the wire has a permanent set of less than 5% when 11% strain is applied to the wire.

According to another example ("Example 21") further to Example 20, the permanent set is less than 1% when the 11% strain is applied to the wire.

According to another example ("Example 22") further to any one of Examples 12 to 21, after the first heat treatment, the wire has a first modulus of less than 42 GPa when 200 MPa of stress is applied to the wire, and after the second heat treatment, the wire has a second modulus of at least 55 GPa when 200 MPa of stress is applied to the wire.

According to another example ("Example 23") further to Example 22, the second modulus is between 55 GPa and 64 GPa.

According to another example ("Example 24") further to any one of Examples 12 to 23, the wire has a lower plateau stress (LPS) of at least 350 MPa.

According to another example ("Example 25") further to any one of Examples 12 to 24, the wire is formed into an implantable medical device.

According to another example ("Example 26") further to Example 25, the medical device is: a stent-graft, an embolic filter, a septal occluder, or a heart valve.

According to another example ("Example 27"), a method of forming a wire of a nickel-titanium alloy includes applying a strain deformation to the wire to set a shape for the wire, applying a first heat treatment to the wire, and applying a second heat treatment to the wire. The first heat treatment including applying heat of a first temperature for a first period of time, and applying the second heat treatment includes applying heat of a second temperature different from the first temperature for a second period of time. The second temperature is between 210° C. and 290° C.

According to another example ("Example 28") further to Example 27, the resulting wire has a LPS of at least 350 MPa after the second heat treatment.

According to another example ("Example 29") further to Example 27 or 28, the second period of time is between 5 minutes and 40 minutes.

According to another example ("Example 30") further to any one of Examples 27 to 29, a first modulus of the wire resulting from the first heat treatment is within 2% of a second modulus of the wire resulting from the second heat treatment.

According to another example ("Example 31") further to any one of Examples 27 to 30, a first elasticity of the wire resulting from the first heat treatment is within 2% of a second elasticity of the wire resulting from the second heat treatment.

According to another example ("Example 32") further to any one of Examples 27 to 31, a second hysteresis of the wire resulting from the second heat treatment is at least 40 MPa lower than a first hysteresis of the wire resulting from the first heat treatment.

According to another example ("Example 33") further to any one of Examples 27 to 32, a second lower plateau stress (LPS) of the wire resulting from the second heat treatment is at least 30 MPa higher than a first LPS of the wire resulting from the first heat treatment.

According to another example ("Example 34") further to any one of Examples 27 to 33, a second permanent set of the wire resulting from the second heat treatment is at least 85% lower than a first permanent set of the wire resulting from the first heat treatment. Each of the first and second permanent sets is defined by a length of the wire after a strain of 11% is applied to the wire.

According to another example ("Example 35") further to any one of Examples 27 to 33, a second permanent set of the wire resulting from the second heat treatment is less than 1%. Each of the first and second permanent sets is defined by a length of the wire after a strain of 11% is applied to the wire.

According to another example ("Example 36") further to any one of Examples 27 to 33, the resulting wire has a permanent set of less than 5% when 11% strain is applied to the wire.

According to another example ("Example 37") further to Example 36, the permanent set is less than 1% when the 11% strain is applied to the wire.

According to another example ("Example 38") further to any one of Examples 27 to 37, after the first heat treatment, the wire has a first modulus of less than 42 GPa when 200 MPa of stress is applied to the wire, and after the second heat treatment, the wire has a second modulus of at least 55 GPa when 200 MPa of stress is applied to the wire.

According to another example ("Example 39") further to Example 38, the second modulus is between 55 GPa and 64 GPa.

According to another example ("Example 40") further to any one of Examples 27 to 39, the resulting wire has a lower plateau stress (LPS) of at least 350 MPa.

According to another example ("Example 41") further to any one of Examples 27 to 40, the method further includes forming the wire into an implantable medical device after the second heat treatment is applied.

According to another example ("Example 42") further to Example 41, the medical device is: a stent-graft, an embolic filter, a septal occluder, or a heart valve.

The foregoing Examples are just that, and should not be read to limit or otherwise narrow the scope of any of the concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

DETAILED DESCRIPTION

Definitions and Terminology

This disclosure is not meant to be read in a restrictive manner. For example, the terminology used in the application should be read broadly in the context of the meaning those in the field would attribute such terminology.

With respect to terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example.

DESCRIPTION OF VARIOUS EMBODIMENTS

Treatment processes are disclosed herein for a wire or wire construct made of nickel-titanium alloy, where the wire is obtained by a cold work process and subsequently undergoes a first heat treatment while strain is applied to the wire to shape-set the wire. The wire further undergoes a second heat treatment following the first heat treatment, where the second heat treatment is performed in a temperature of between 210° C. and 290° C.

The disclosed treatment processes enable the wire to have one or more advantageous physical property or properties. For example, the wire which has undergone the second heat treatment process has one or more of: an increased lower plateau stress (LPS), a decreased hysteresis, and/or a decreased permanent set, as compared with a wire that is formed using other prior-known processes, as detailed herein below. Additionally, in some examples, the wire obtained through the disclosed treatment processes is more capable of superelastic recovery than the wire formed with prior-known processes.

Figure 1:
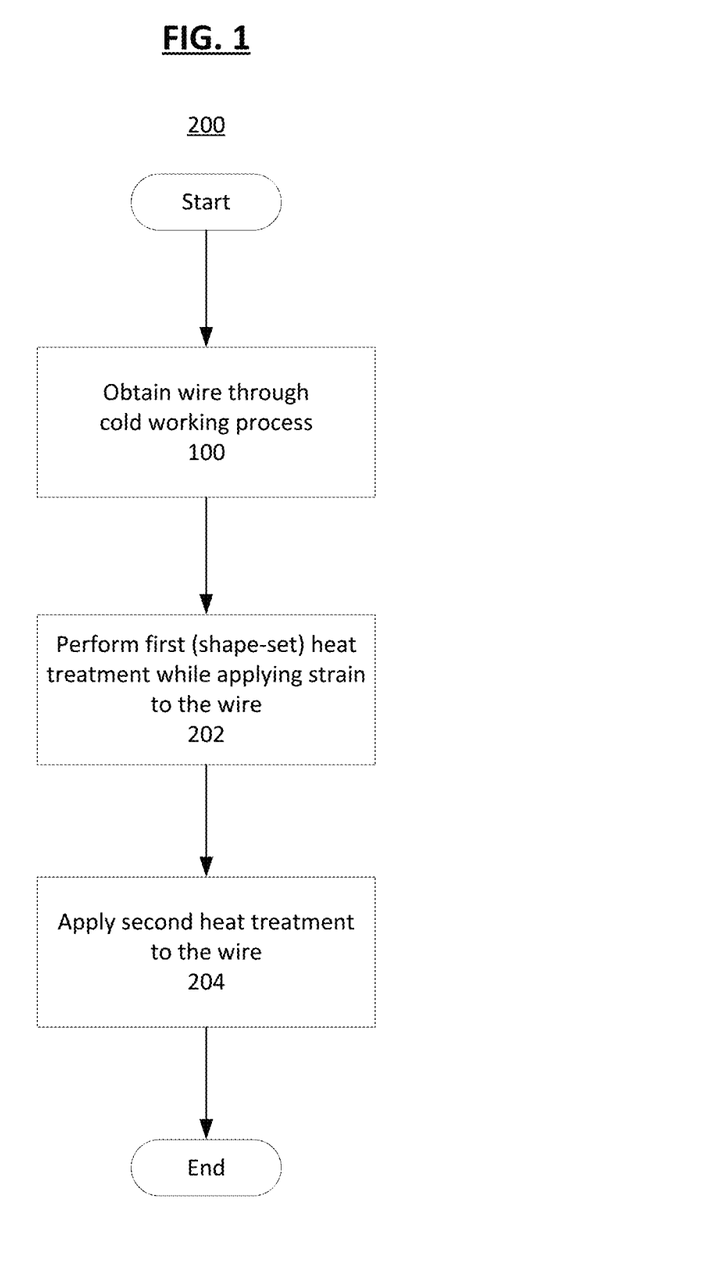
FIG. 1 shows a flow diagram of a process for applying heat treatments to form a wire according to an embodiment disclosed herein.

FIG. 1 shows a treatment process 200 for a wire or wire construct made of nickel-titanium alloy according to an embodiment disclosed herein. In a first step 100 of the process 200, a wire that has gone through cold working is obtained. Note that the step 100 may include any cold working process as known in the art; such process is called "cold working" because it involves shaping the metal below its recrystallization temperature. In some examples, the cold working process may be performed at room temperature.

In a second step 202 of the process 200 following step 100, a first heat treatment is applied to the wire to permanently shape set the wire in the desired geometry while strain is applied to the wire. The first heat treatment includes applying heat of a first temperature for a first period of time. The first temperature can be between 450° C. and 550° C. in some examples. In other examples, the first temperature can be from 450° C. to 470° C., 470° C. to 500° C., 500° C. to 520° C., 520° C. to 550° C., or any other range therebetween. In some examples, the first heat treatment may include one or more additional heating processes to set the shape for the wire.

In step 204, a second heat treatment is applied to the wire, where the second heat treatment includes applying heat of a second temperature different from the first temperature for a second period of time. In some examples, the second temperature being between 210° C. and 290° C. In some examples, the second heat treatment is in the temperature range of from 210° C. to 220° C., 220° C. to 230° C., 230° C. to 240° C., 240° C. to 250° C., 250° C. to 260° C., 260° C. to 270° C., 270° C. to 280° C., 280° C. to 290° C., or any range or combination thereof. In some examples, the second heat treatment is effective when in the time length range of from 5 to 15 minutes, 15 to 30 minutes, 30 to 40 minutes, or any range or combination thereof.

During each of the aforementioned steps, the physical properties of the wire undergo changes, such as in the physical properties including modulus, permanent set, recoverable strain, plateau stresses, as well as other properties as discussed further herein. These properties are measured using a testing method known as ASTM F2516 Standard Test Method for Tension Testing of Nickel-Titanium Superelastic Materials. In the ASTM F2516 method, a sample of nitinol wire is loaded by securing the two ends of the wire in fixtures of a measuring apparatus. After the wire is securely fixed to the measuring apparatus, the two ends of the wire are pulled farther away from each other at a specified rate until the wire reaches a specified strain percentage. In some examples, this specified strain percentage is 6% of the length of the wire. Then, the direction of the movement of the two ends of the wire is reversed such that the two ends are brought closer to each other until the load reaches below a predetermined limit. Lastly, the two ends of the wire are pulled apart again, this time until the wire breaks. The measurements taken at each step are used to make a stress-strain curve that represents the physical properties of the nitinol being tested. An example of such stress-strain curve is shown in FIG. 2.

Figure 2:
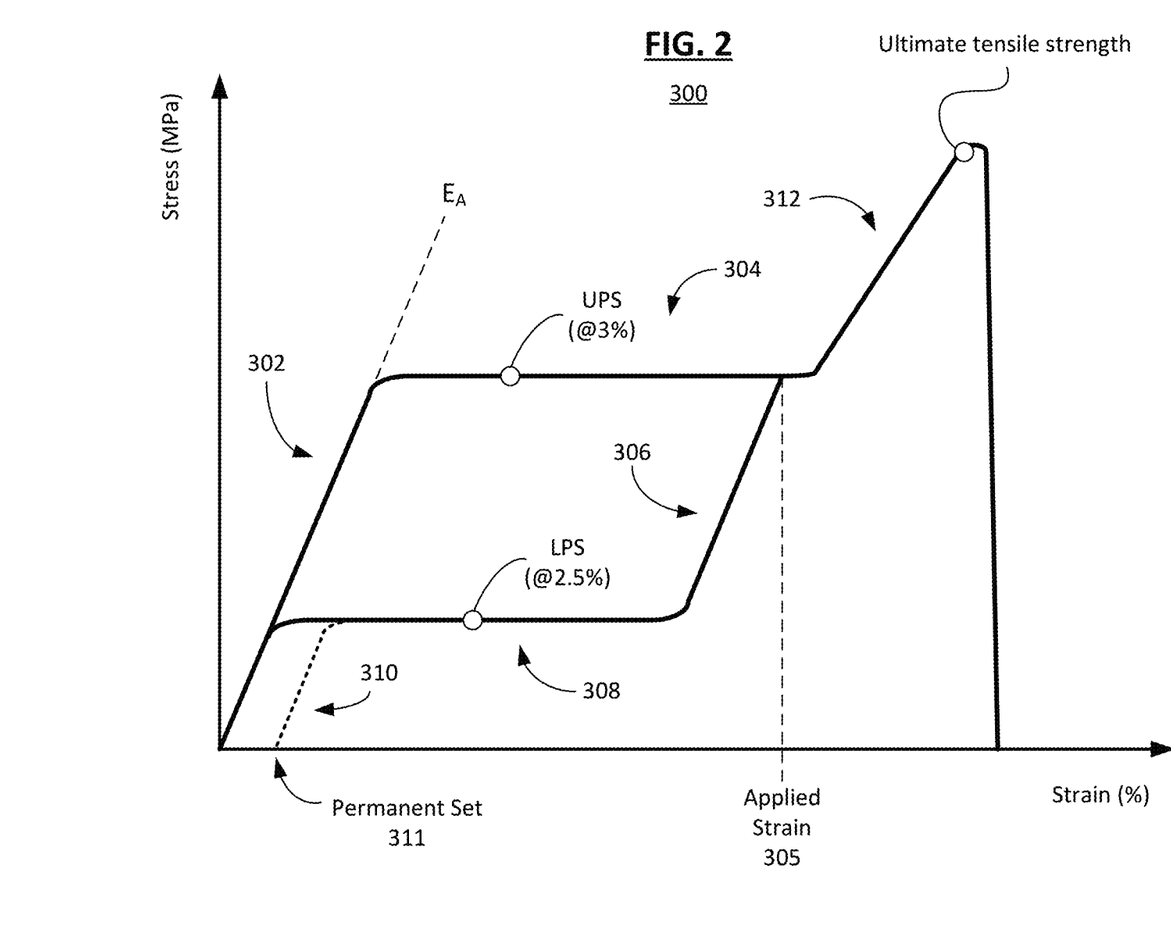
FIG. 2 shows an example of a stress-strain curve of a wire formed in an embodiment according to the method disclosed herein.

FIG. 2 shows an example stress-strain curve 300 which include some of the characteristics of the nitinol wire that can be determined using the ASTM F2516 method. Firstly, when the initial strain is applied to the wire by pulling the two ends in opposite directions, the wire undergoes linear elastic (non-permanent) deformation 302 with a slope of $E_A$ (i.e. Young's modulus or elastic modulus) defining the ratio of tensile stress (in Pascals) to tensile strain (in % change in length). Then, the tensile stress experiences a flat region or plateau 304 in which the wire undergoes tensile strain without additional stress applied to it. According to the specification of the ASTM F2516 method, an upper plateau stress (UPS) is defined as the stress measured in this plateau 304, more particularly at 3% strain when the tensile stress is initially applied. Then, according to the specification of the ASTM F2516 method, the tensile stress is applied until the strain reaches an applied strain 305, which according to the ASTM F2516 specification is 6%, which is the initial load strain or a recoverable (i.e., reversible) strain for testing nitinol, after which the direction is reversed during an unloading process 306 which brings the two ends of the wire closer together. The wire undergoes another plateau 308 in this process, and LPS is measured, according to the specification of the ASTM F2516 method, at 2.5% strain after the wire reaches the initial 6% strain. The difference between the values for the UPS and LPS is defined as mechanical hysteresis. It should be noted that for different values of the applied strain 305, different amounts of permanent set 311 are observed. A permanent set 311 is defined by a length of the wire after the strain 305 is applied to the wire and subsequently unstrained. When the resulting length of the wire after unstraining is longer than the initial length of the wire, the difference in lengths determines the amount of permanent set 311 that the wire has undergone. The smaller the increase is in the length of the wire, the lesser the amount of permanent set 311 therein, which indicates that the wire is more capable of superelastic recovery.

Thereafter, the wire has 5 MPa of stress being applied thereto, according to the specification of the ASTM F2516 method. In the absence of any other stress, the wire may return to the initial length. In many nitinol wires, the length of the wire does not change or change very little, for example less than 0.5% change in the length before and after the initial strain of 6% is reached, but in some cases, the resulting length of the wire is longer than the initial length. In these case, the wire is said to have undergone a permanent deformation 310 with a permanent set 311 that is determined by comparing the resulting length of the wire with the initial length. Lastly, the two ends of the wire are pulled in opposite direction again such that the wire undergoes the elastic deformation 302 and the upper plateau 304. However, this time, the wire is pulled past the 6% strain and undergoes plastic (permanent) deformation 312, after which the wire breaks, or fractures, when the wire is at an ultimate permanent set, to measure an ultimate tensile strength (UTS) of the wire.

In a conventional process that causes a wire of nickel-titanium alloy to obtain its physical properties, the wire undergoes strain deformation to be shaped into a desired form, and subsequently undergoes a shape set annealing process through a heat treatment at a temperature commonly used for shape setting. Examples of methods that are used to process a nitinol wire are disclosed below as well as the resulting properties of each wire prepared using the process. The first example ("Example Process 1") pertains to the method of wire treatment known in the art, and the second example ("Example Process 2") pertains to the present disclosure. The method in Example Process 2 show below is exemplary and not limiting; further uses will be recognized by a skilled artisan.

Example Process 1: A nitinol wire (for example: a superelastic ASTM F2063 compliant wire of 0.0206" wire diameter) is obtained, which was prepared via a cold working process and reduced to a 0.0206" wire diameter. Specifically, the nitinol wire undergoes the drawing process at room temperature (approximately 25° C.) which is well below the recrystallization temperature (e.g., 550° C.) of the wire. Then, after strain deformation is applied, the wire undergoes a shape set annealing process in which the wire is heated to a temperature typically used for shape setting (e.g., 470° C.) of the alloy and below the melting temperature (1310° C.), maintaining the wire in the temperature for an amount of time, and then cooling the wire back to room temperature. In this example, the wire underwent a shape set annealing process at 470° C. for 17 minutes and resulted in having the permanent set 311 of 5.6% after the applied strain 305 of 11%.

Example Process 2: A nitinol wire undergoes a first heat treatment under step 202 of process 200, where the first heat treatment is performed at 470° C., which is the shape setting temperature of the wire, for a length of 17 minutes, which are the same temperature and time as the above shape set annealing process in Example Process 1. The wire is shape set into straight sections by applying strain and held in shape during the annealing process (step 202) during the first heat treatment, after which a second heat treatment is applied to the wire in step 204, where the second heat treatment involves a temperature lower than the first heat treatment. The second heat treatment in one example involves maintaining the wire at 250° C. for 40 minutes. In this example, the wire resulted in having the permanent set 311 of 0.6% after the applied strain 305 of 11%.

Figure 3:
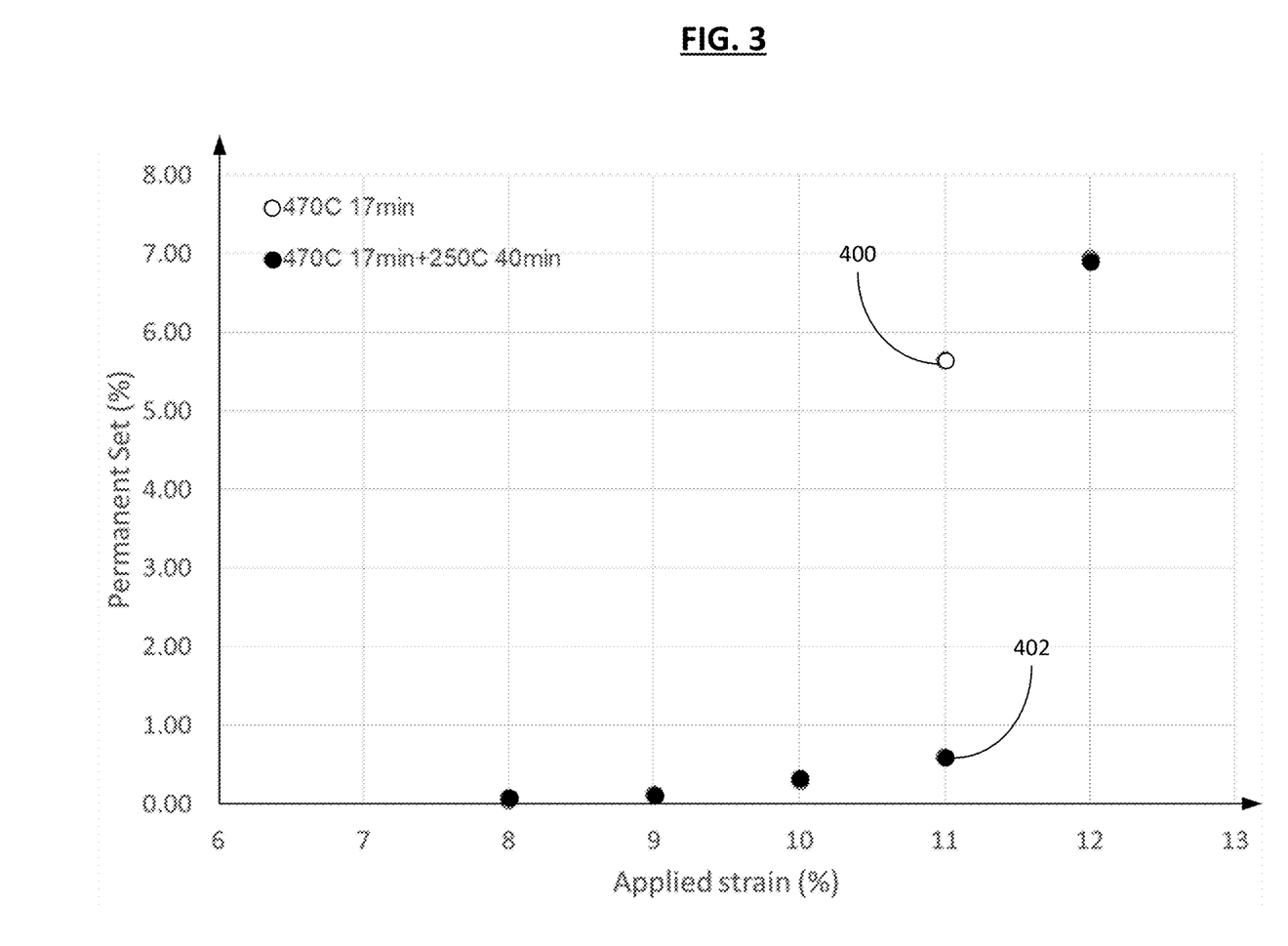
FIG. 3 shows an applied strain vs permanent set graph for wires formed using different heat treatment processes according to an embodiment disclosed herein.

FIG. 3 compares the different permanent sets 311 that the same type of nitinol wire resulted in having after different amounts of applied strain 305 in Example Processes 1 and 2. In the figure, especially at the applied strain 305 of 11%, a first sample 400 which is based on the procedure performed in Example Process 1 (that is, undergoing only the first heat treatment at 470° C.) has the permanent set 311 of 5.6% which is higher than in a second sample 402 which is based on the procedure performed in Example Process 2 (that is, undergoing the first heat treatment at 470° C. and a second heat treatment at 250° C.) and has the permanent set 311 of 0.6%. In this example, there is an 89% reduction in the permanent set 311 from the first sample 400 to the second sample 402. Therefore, because there is reduced permanent set 311 in the second sample 402 as compared to the first sample 400, the second sample 402 can be said to have greater superelastic recovery than the first sample 400. In some examples, the applied strain 305 is between 10.5% and 11.5%. In some examples, the second heat treatment using a temperature between 210° C. and 290° C. causes the wire to experience a permanent set reduction of at least 50%, 60%, 70%, 80%, 85%, or any range therebetween, compared to the wire which underwent only the first heat treatment.

Example Process 3: A nitinol wire undergoes a first heat treatment under step 202 of process 200, where the first heat treatment is performed at 470° C., which is the shape setting temperature of the wire, for a length of 17 minutes, which are the same temperature and time as the above shape set annealing process in Example Process 1. A strain deformation is applied to the wire in during the first heat treatment in step 202, after which a second heat treatment is applied to the wire in step 204, where the second heat treatment involves a temperature lower than the first heat treatment. The second heat treatment involves maintaining the wire at 320° C. for 40 minutes. In this example, the wire resulted in having the permanent set 311 of 6.0% after the applied strain 305 of 11%.

Figure 4:
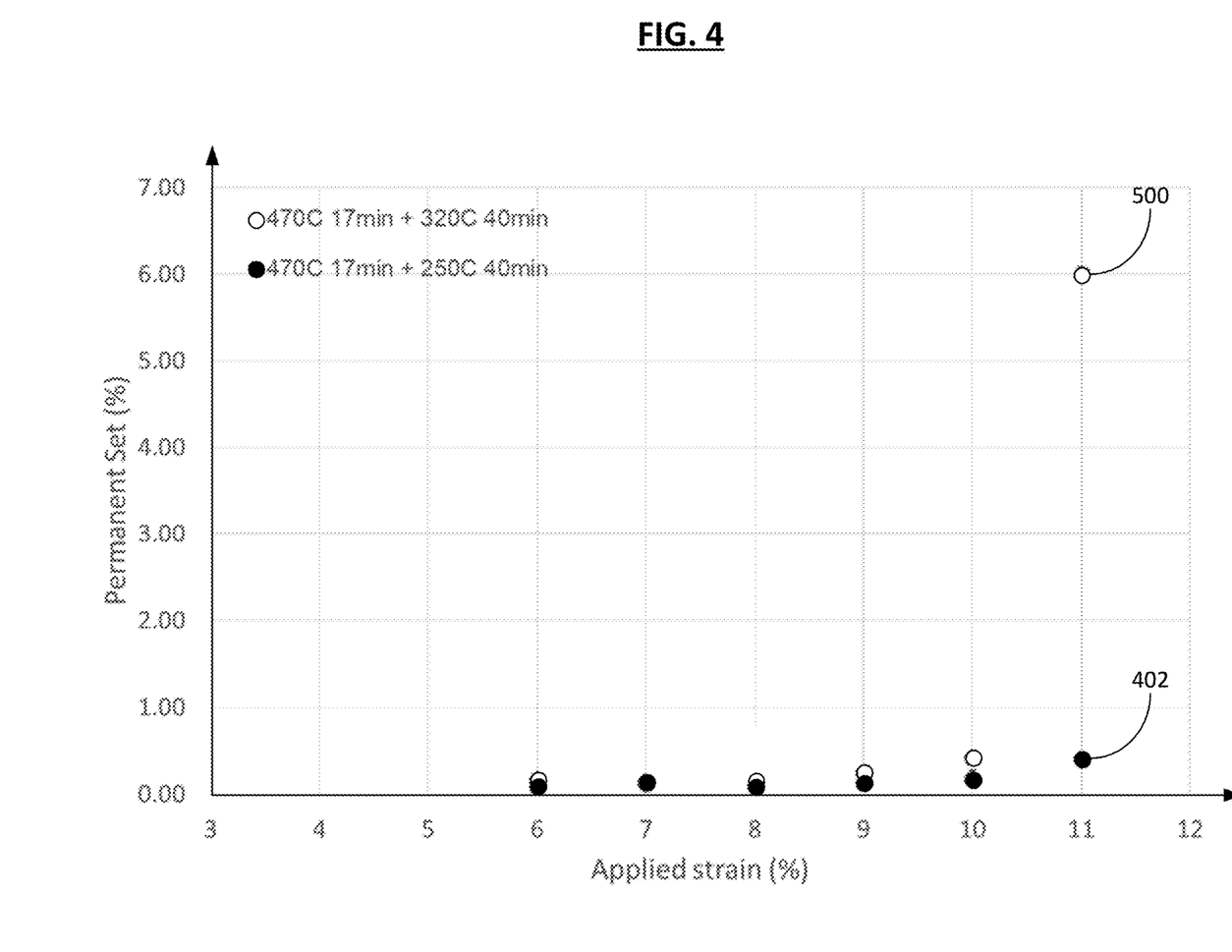
FIG. 4 shows an applied strain vs permanent set graph for wires formed using different heat treatment processes according to an embodiment disclosed herein.

FIG. 4 compares the different permanent sets 311 that the same type of nitinol wire resulted in having after different amounts of applied strain 305 in Example Processes 2 and 3. In the figure, especially at the applied strain 305 of 11%, the second sample 402 from FIG. 3, which is based on the procedure performed in Example Process 2, has the permanent set 311 of 0.4% which is lower than a third sample 500 which is based on the procedure performed in Example Process 3, having the permanent set 311 of 6.0%. Because there is a reduced permanent set 311 in the second sample 402 with respect to the third sample 500, the second sample 402 can be said to have greater superelastic recovery than the third sample 500. In some examples, the applied strain 305 is between 10.5% and 11.5%. Therefore, when the wire undergoes a second heat treatment at a temperature beyond the range of between 210° C. and 290° C., the permanent set 311 increases, causing less superelastic recovery in the wire, as compared to the wire which underwent the second heat treatment at a temperature within the range of between 210° C. and 290° C.

In view of the results of FIGS. 3 and 4, there is a certain region of temperature range for the second heat treatment where the second heat treatment appears to be particularly effective in increasing the elasticity of the wire at 11%, for example. Example Process 3 shows the wire experiencing the permanent set 311 of 6.0% after the applied strain 305 of 11%, which is similar to Example Process 1 in which the wire experienced the permanent set 311 of 5.6% after the same applied strain 305, even though Example Process 3 underwent the second heat treatment as in Example Process 2. Some examples of such regions are explained elsewhere herein. Also, in some examples, when the wire undergoes the second heat treatment with the temperature between 210° C. and 290° C., the second sample 402 achieves a permanent set of less than 5%, less than 4%, less than 3%, less than 2%, less than 1%, less than 0.9%, less than 0.8%, less than 0.7%, less than 0.6%, less than 0.5%, or any range therebetween, a strain 305 of 11% is applied to the wire.

Furthermore, in some examples, the wire after undergoing the second heat treatment in the temperature and time length range as explained above also has the UPS 304 of at least 630 MPa and the LPS 308 of at least 345 MPa. Specifically, in one example involving the first heat treatment of 450° C. and the second heat treatment of 250° C., an average UPS 304 value of 641.31 MPa and an average LPS 308 value of 352.54 MPa were observed, resulting in a hysteresis, or a difference between the UPS 304 and the LPS 308, of 288.77 MPa.

Other examples with differing (or nonexistent) second heat treatment temperatures are shown below in Table 1, which show that having the second heat treatment fall within the specified temperature range increases the LPS 308 as well as the hysteresis of the wire. Also shown in Table 1 are the increase observed in the LPS 308 as well as the decrease in hysteresis after the second heat treatment as compared to the example where only the first heat treatment was performed.

TABLE 1

Condition vs UPS/LPS/Hysteresis - the condition indicates the two (or one in the first example) heat treatment temperatures as well as the resulting UPS, LPS, and hysteresis.

| Condition (° C.) | UPS (MPa) | LPS (MPa) | LPS change w.r.t. 450 only (MPa) | Hysteresis = UPS − LPS (MPa) | Hysteresis change w.r.t. 450 only (MPa) |
|---|---|---|---|---|---|
| 450 only | 649.46 | 318.87 | 0 | 330.59 | 0 |
| 450 then 100 | 647.87 | 334.47 | +15.6 | 313.4 | −17.19 |
| 450 then 250 | 641.31 | 352.54 | +33.67 | 288.77 | −41.82 |
| 450 then 320 | 625.02 | 325.19 | +6.32 | 299.83 | −30.76 |

According to Table 1, the wire undergoing the second heat treatment always results in a higher LPS and lower hysteresis compared to just undergoing the first heat treatment. At the minimum, the second heat treatment causes a 6 MPa increase in the LPS and a 17 MPa decrease in the hysteresis. The temperature at which the second heat treatment is performed also affects the values, as shown in the fact that among the three temperatures being used, the 250° C. second heat treatment temperature causes the greatest change, as well as having the highest LPS and the lowest hysteresis among all conditions, including the one where only the first heat treatment is performed. As such, in some examples, the increase in the LPS resulting from the second heat treatment is at least 15 MPa or 30 MPa, and the decrease in the hysteresis resulting therefrom is at least 30 MPa or 40 MPa. In some examples, the temperature range of between 210° C. and 290° C. of the second heat treatment causes at least 30 MPa increase in the LPS and at least 40 MPa decrease in the hysteresis, as compared to when only the first heat treatment is applied. Also, this temperature range causes the LPS to increase, to at least 350 MPa.

In some examples, a secondary component may be attached to the wire, such as, but not limited to, via thermal bonding and suturing. The secondary component may be made of polymeric material including, but not limited, to bioabsorbable polymers (such as polylactic acid, poly(trimethylene carbonate) or PGA/TMC), fluoropolymers (such as fluorinated ethylene propylene or FEP, polytetrafluoroethylene or PTFE and expanded fluoropolymers, such as expanded polytetrafluoroethylene or ePTFE), fluoroelastomers and elastomeric materials (for example, TFE/PMVE copolymers), polyesters (such as polyethylene terephthalate or PET), polyethylenes, polypropylenes, polyurethanes, or silicones, for example. Additionally or alternatively, the second heat treatment may be used to cure or modify a secondary component associated with the wire (e.g., a drug coating, therapeutic, or other material). The secondary component may be a graft member or other component of a stent graft, a heart valve leaflet, skirt, cuff, or other component of a heart valve, a filter membrane or other component of a filter, or other secondary component as desired.

Additionally, in some examples, a first modulus of the wire resulting from the first heat treatment is approximately the same as a second modulus of the wire resulting from the second heat treatment. That is, the wire after the second heat treatment retains the same ratio of tensile stress to tensile strain as it did after the first heat treatment. In some other examples, the second modulus measured after the second heat treatment remains within a 2% range (i.e., increases or decreases by less than 2%) from the first modulus measured after the first heat treatment. In some examples, a first elasticity of the wire resulting from the first heat treatment is approximately the same as a second elasticity of the wire resulting from the second heat treatment. In other examples, the second elasticity is within a 2% range from the first elasticity.

Figure 5:
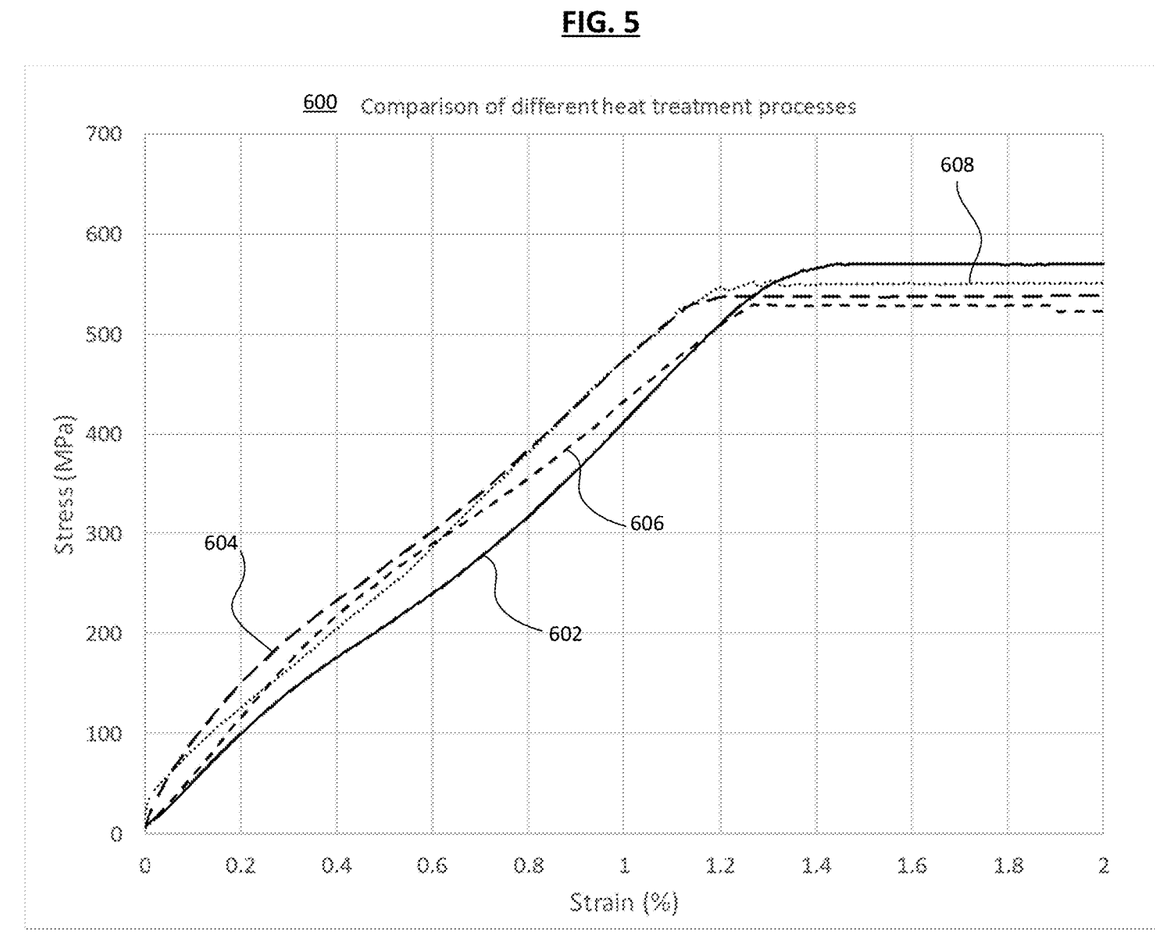
FIG. 5 shows a graph comparing the different strain vs stress curves obtained from different heat treatment processes as known in the art and according to embodiments as disclosed herein.

FIG. 5 is a graph 600 comparing the experimental data of the different stress vs strain curves as observed in a wire that undergoes one of four heat treatment processes. In a first process 602, shown on the graph 600 as a solid line, the wire is heated at the first heat treatment temperature of 470° C. for 17 minutes, followed by the second heat treatment temperature of 320° C. at 40 minutes. In a second process 604, shown on the graph 600 as a broken line with longer segments, the wire is heated at the first heat treatment temperature of 470° C. for 17 minutes, followed by the second heat treatment temperature of 270° C. for 40 minutes. In a third process 606, shown on the graph 600 as a broken line with shorter segments, the wire is heated at the first heat treatment temperature of 470° C. for 17 minutes, followed by the second heat treatment temperature of 210° C. for 40 minutes. In a fourth process 608, shown on the graph 600 as a dotted line, the wire is heated only at the first heat treatment temperature of 470° C. for 17 minutes, without any subsequently heat treatment.

The resulting data are gathered such that for each of the four processes mentioned above, the wire undergoes different values of stress loading (in MPa) to measure the amount of strain (in % of original wire length) is caused by each load of stress. The data are plotted as shown on FIG. 5, and then analyzed to determine the modulus (in GPa) which is calculated by dividing the stress by the corresponding stress. In the tables shown below, the modulus is calculated at 200 MPa and 400 MPa of applied stress.

TABLE 2

Comparison of the moduli for the first and second processes, at 200 and 400 MPa, as well as the difference between the calculated moduli.

| First Process 602 | | | Second Process 604 | | |
|---|---|---|---|---|---|
| Stress (MPa) | Strain (%) | Modulus (GPa) | Stress (MPa) | Strain (%) | Modulus (GPa) |
| 200 | 0.48 | 41.67 | 200 | 0.32 | 63.25 |
| 400 | 0.97 | 41.24 | 400 | 0.84 | 47.69 |
| Change in modulus between 200 & 400 MPa: | | 0.43 | Change in modulus between 200 & 400 MPa: | | 15.56 |

TABLE 3

Comparison of the moduli for the first and second processes, at 200 and 400 MPa, as well as the difference between the calculated moduli.

| Third Process 606 | | | Fourth Process 608 | | |
|---|---|---|---|---|---|
| Stress (MPa) | Strain (%) | Modulus (GPa) | Stress (MPa) | Strain (%) | Modulus (GPa) |
| 200 | 0.36 | 55.56 | 200 | 0.38 | 52.63 |
| 400 | 0.91 | 43.96 | 400 | 0.83 | 48.19 |
| Change in modulus between 200 & 400 MPa: | | 11.60 | Change in modulus between 200 & 400 MPa: | | 4.44 |

As can be observed from the above Tables 2 and 3, the second and third processes 604 and 606 cause greater change in modulus between 200 MPa and 400 MPa. In fact, the second and third processes 604 and 606, which include the second heat treatment within the specified range of temperatures as disclosed herein, have greater moduli at 200 MPa of applied stress. More specifically, the measured moduli range from at least 53 GPa, at least 54 GPa, or at least 55 GPa, etc. In some examples, the measured moduli range between 53 GPa and 64 GPa, 55 GPa and 64 GPa, 57 GPa and 64 GPa, 60 GPA and 64 GPa, 62 GPa and 64 GPa, or any range therebetween. In comparison, the first process 602 has the lowest modulus at 41.67 GPa, and the fourth process at 52.63 GPa, both of which are below the moduli of the second and third processes 604 and 606.

Also, the change in moduli of the second and third processes 604 and 606 is greater than 5 GPa, greater than 7 GPa, or greater than 10 GPa, etc., between the applied stresses at 200 MPa and 400 MPa. In some examples, the change in moduli of the second and third processes 604 and 606 is between 5 GPa and 16 GPa, 7 GPa and 16 GPa, 10 GPa and 16 GPa, 12 GPa and 16 GPa, 14 GPa and 16 GPa, or any range therebetween. In comparison, the first process 602 has 0.43 GPa of change in modulus, whereas the fourth process 608 has 4.44 GPa, well below those of the second and third processes 604 and 606.

FIGS. 6A to 6D illustrate examples of various implantable medical devices which may be made using the wire as disclosed herein. The wire may be formed into any one or more of these medical devices using any suitable method known in the art. The examples are merely illustrative and are not meant to be exhaustive, and the shapes and configurations of the medical devices are not limited to those shown in the figures.

Figure 6A:
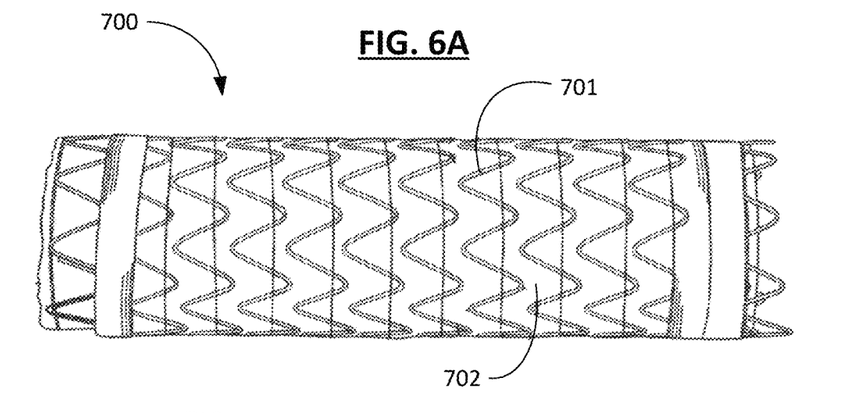
FIGS. 6A through 6D show examples of implantable medical devices which may be formed using the wire(s) as disclosed herein according to various embodiments.

FIG. 6A shows an example of a stent-graft 700 which includes one or more wire or stent 701 and one or more membranous material or graft 702. The wire or stent 701 may be helically formed surrounding the graft 702, although any suitable configuration may be envisioned.

Figure 6B:
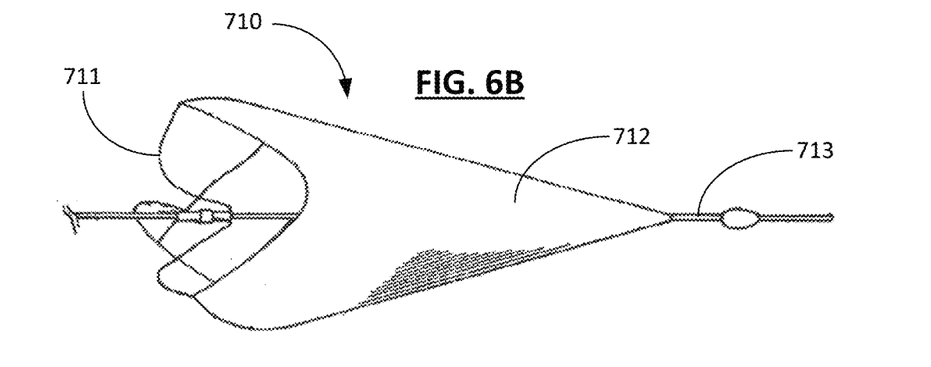

FIG. 6B shows an example of an embolic filter 710 which includes wires or struts 711 and one or more membranous material or filter element 712, which are affixed to a central support member 713. The struts 711 may be straight, curved, or have any other suitable shape and configuration.

Figure 6C:
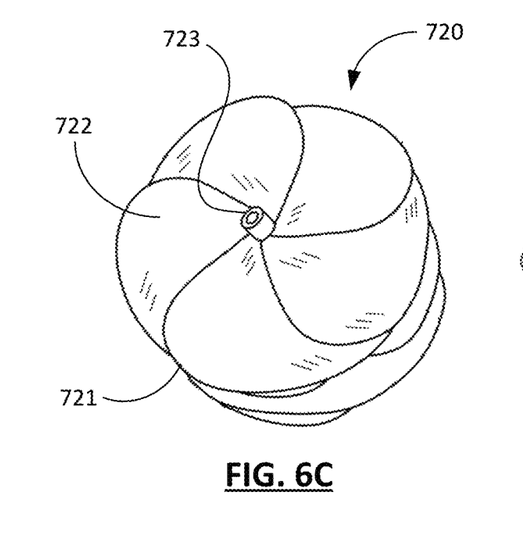

FIG. 6C shows an example of a septal occluder or cardiac sealing device 720 which includes one or more wire forming a wire frame 721, one or more membranous material or sealing member 722, and one or more eyelet 723 which may or may not be occluded to control fluid flow therethrough. The wire frame 721 may be attached to or implemented with the eyelet 723 and the sealing member 722 may be attached to the wire frame 721. The wire frame 721 may assume any suitable configuration as known in the art.

Figure 6D:
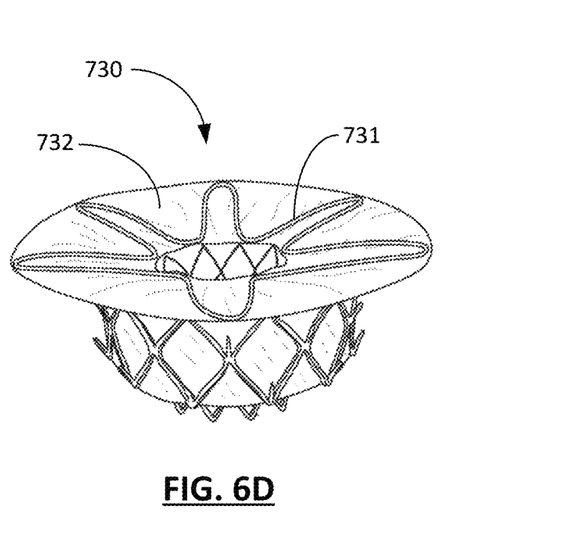

FIG. 6D shows an example of a heart valve or prosthetic retention element 730 which includes one or more wire forming a valve frame 731 and one or more membranous material or cover 732. The cover 732 may be attached to or implemented with the valve frame 731. The valve frame 731 may assume any suitable configuration as known in the art.

The embodiments and methods disclosed herein may also be used to enable a variety of shape memory articles. The shape memory articles may include medical devices such as implantable medical devices. The implantable medical devices may be devices of nitinol shape memory alloy, such as one that is superelastic at normal body temperature (approximately 37° C.). Implantable medical devices are defined as devices that are intended to remain within a living body for periods of 24 hours or longer.

The medical devices or articles may be produced from materials of various shapes, such as wire of various transverse cross sectional shapes including circular, elliptical, square, rectangular, etc. Alternatively, the devices or articles may be made by machining precursor forms such as sheets, tubes or rods, as by electrical discharge machining (EDM), laser cutting, chemical milling, or the like.

The disclosure of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this disclosure provided they come within the scope of the appended claims and their equivalents.

What is claimed is:

1. A wire of a nickel-titanium alloy having a permanent set of less than 5% in length when 11% strain is applied to the wire, the wire having a modulus of at least 53 GPa when 200 MPa of stress is applied to the wire, wherein the modulus is calculated based on a tensile stress and a tensile strain of the wire.

2. The wire of claim 1, wherein the permanent set is less than 1% when the 11% strain is applied to the wire.

3. The wire of claim 1, wherein the modulus is at least 55 GPa.

4. The wire of claim 1, wherein the modulus is between 53 GPa and 64 GPa.

5. The wire of claim 1, wherein the modulus decreases by at least 5 GPa when 400 MPa of stress is applied to the wire.

6. The wire of claim 5, wherein the modulus decreases by at least 10 GPa when 400 MPa of stress is applied to the wire.

7. The wire of claim 5, wherein the modulus decreases by a value of between 5 GPa and 16 GPa when 400 MPa of stress is applied to the wire as compared to when 200 MPa of stress is applied to the wire.

8. The wire of claim 1, further having a lower plateau stress (LPS) of at least 350 MPa, wherein the LPS is measured in response to applying a reversible strain to the wire.

9. The wire of claim 1, further formed into an implantable medical device.

10. The wire of claim 9, wherein the medical device is: a stent-graft, an embolic filter, a septal occlude, or a heart valve.

11. A wire of nickel-titanium alloy formed by a method comprising:
    applying a first heat treatment to the wire, the first heat treatment including applying heat of a first temperature between 450° C. and 550° C. for a first period of time;
    applying, during the first heat treatment, a strain deformation to the wire to set a shape for the wire; and
    applying a second heat treatment to the wire following the first heat treatment without applying the strain deformation between the first heat treatment and the second heat treatment, or during the second heat treatment, the second heat treatment includes applying heat of a second temperature different from the first temperature for a second period of time, the second temperature being between 210° C. and 290° C.

12. The wire of claim 11, wherein the first heat treatment further comprises one or more additional heat treatment processes operable to set a shape of the wire.

13. The wire of claim 11, wherein the second period of time is between 5 minutes and 40 minutes.

14. The wire of claim 11, wherein a first elasticity of the wire resulting from the first heat treatment is within 2% of a second elasticity of the wire resulting from the second heat treatment.

15. The wire of claim 11, wherein a second hysteresis of the wire resulting from the second heat treatment is at least 40 MPa lower than a first hysteresis of the wire resulting from the first heat treatment.

16. The wire of claim 11, wherein a second lower plateau stress (LPS) of the wire resulting from the second heat treatment is at least 30 MPa higher than a first LPS of the wire resulting from the first heat treatment.

17. The wire of claim 11,
    wherein a second permanent set of the wire resulting from the second heat treatment is at least 85% lower than a first permanent set of the wire resulting from the first heat treatment, and
    wherein each of the first and second permanent sets is defined by a length of the wire after a strain of 11% is applied to the wire.

18. The wire of claim 11 having a permanent set of less than 5% in length when 11% strain is applied to the wire.

19. The wire of claim 18, wherein the permanent set is less than 1% when the 11% strain is applied to the wire.

20. The wire of claim 11, wherein after the first heat treatment, the wire has a first modulus of less than 42 GPa when 200 MPa of stress is applied to the wire, and after the second heat treatment, the wire has a second modulus of at least 55 GPa when 200 MPa of stress is applied to the wire.

21. The wire of claim 20, wherein the second modulus is between 55 GPa and 64 GPa.

22. The wire of claim 11, further having a lower plateau stress (LPS) of at least 350 MPa.

23. The wire of claim 11, further formed into an implantable medical device.

24. The wire of claim 23, wherein the medical device is: a stent-graft, an embolic filter, a septal occlude, or a heart valve.

25. A method of forming a wire of a nickel-titanium alloy, the method comprising:
    applying a strain deformation to the wire to set a shape for the wire;
    applying a first heat treatment to the wire following the applying the strain deformation, the first heat treatment including applying heat of a first temperature between 450° C. and 550° C. for a first period of time; and
    applying a second heat treatment to the wire following the first heat treatment without applying the strain deformation between the first heat treatment and the second heat treatment, or during the second heat treatment, wherein applying the second heat treatment includes applying heat of a second temperature different from the first temperature for a second period of time, the second temperature being between 210° C. and 290° C.

26. The method of claim 25, resulting with a wire having a LPS of at least 350 MPa after the second heat treatment.

27. The method of claim 25, wherein the second period of time is between 5 minutes and 40 minutes.

28. The method of claim 25, wherein a first modulus of the wire resulting from the first heat treatment is within 2% of a second modulus of the wire resulting from the second heat treatment.

29. The method of claim 25, wherein a first elasticity of the wire resulting from the first heat treatment is within 2% of a second elasticity of the wire resulting from the second heat treatment.

30. The method of claim 25, wherein a second hysteresis of the wire resulting from the second heat treatment is at least 40 MPa lower than a first hysteresis of the wire resulting from the first heat treatment.

31. The method of claim 25, wherein a second lower plateau stress (LPS) of the wire resulting from the second heat treatment is at least 30 MPa higher than a first LPS of the wire resulting from the first heat treatment.

32. The method of claim 25,
    wherein a second permanent set of the wire resulting from the second heat treatment is at least 85% lower than a first permanent set of the wire resulting from the first heat treatment,
    wherein each of the first and second permanent sets is defined by a length of the wire after a strain of 11% is applied to the wire.

33. The method of claim 25,
    wherein a second permanent set of the wire resulting from the second heat treatment is less than 1%,
    wherein each of the first and second permanent sets is defined by a length of the wire after a strain of 11% is applied to the wire.

34. The method of claim 25, wherein the resulting wire has a permanent set of less than 5% in length when 11% strain is applied to the wire.

35. The method of claim 34, wherein the permanent set is less than 1% when the 11% strain is applied to the wire.

36. The method of claim 25, wherein after the first heat treatment, the wire has a first modulus of less than 42 GPa when 200 MPa of stress is applied to the wire, and after the second heat treatment, the wire has a second modulus of at least 55 GPa when 200 MPa of stress is applied to the wire.

37. The method of claim 36, wherein the second modulus is between 55 GPa and 64 GPa.

38. The method of claim 25, wherein the resulting wire has a lower plateau stress (LPS) of at least 350 MPa.

39. The method of claim 25, further comprising forming the wire into an implantable medical device after the second heat treatment is applied.

40. The method of claim 39, wherein the medical device is: a stent-graft, an embolic filter, a septal occlude, or a heart valve.

* * * * *